United States Patent
O'Brien

(10) Patent No.: US 7,763,038 B2
(45) Date of Patent: Jul. 27, 2010

(54) SUTURE NEEDLE RETENTION DEVICE

(76) Inventor: Todd O'Brien, 20 Oak View La., West Enfield, ME (US) 04493

( * ) Notice: Subject to any disclaimer, the term of this patent is extended or adjusted under 35 U.S.C. 154(b) by 1264 days.

(21) Appl. No.: 11/298,372

(22) Filed: Dec. 9, 2005

(65) Prior Publication Data

US 2007/0135824 A1 Jun. 14, 2007

(51) Int. Cl.
*A61B 17/04* (2006.01)
*A41H 17/00* (2006.01)
*A61B 17/06* (2006.01)
*A61B 17/70* (2006.01)
*A61M 5/32* (2006.01)

(52) U.S. Cl. .................... 606/148; 223/109 R

(58) Field of Classification Search ............ 606/148, 606/147, 139, 144, 145, 146, 150, 158, 192, 606/210, 222, 263; 206/266, 265, 363, 365, 206/339; 223/109 R; 224/219
See application file for complete search history.

(56) References Cited

U.S. PATENT DOCUMENTS

| | | | | |
|---|---|---|---|---|
| 919,138 A | * | 4/1909 | Drake | 606/144 |
| 3,120,847 A | * | 2/1964 | Caveness | 606/147 |
| 3,353,203 A | * | 11/1967 | Ginter | 15/244.1 |
| 3,500,829 A | * | 3/1970 | Abramowitz | 604/170.01 |
| 3,727,658 A | | 4/1973 | Eldridge, Jr. | |
| 3,878,848 A | * | 4/1975 | Hiebert | 606/148 |
| 3,933,286 A | * | 1/1976 | Karkas | 224/219 |
| 3,944,069 A | | 3/1976 | Eldridge, Jr. | |
| 3,946,740 A | * | 3/1976 | Bassett | 606/145 |
| 3,951,261 A | | 4/1976 | Mandel et al. | |
| 4,008,802 A | | 2/1977 | Freitag | |
| 4,243,140 A | | 1/1981 | Thrun | |
| 4,287,987 A | | 9/1981 | Hoffman et al. | |
| 4,380,292 A | | 4/1983 | Cramer | |
| 4,418,821 A | | 12/1983 | Sandel | |
| 4,717,386 A | | 1/1988 | Simmons | |
| 4,755,170 A | * | 7/1988 | Golden | 604/513 |
| 4,969,893 A | | 11/1990 | Swor | |
| 5,209,738 A | * | 5/1993 | Bruno | 604/192 |
| 5,342,375 A | * | 8/1994 | Lemole | 606/148 |
| 5,454,823 A | * | 10/1995 | Richardson et al. | 606/148 |
| 5,470,338 A | * | 11/1995 | Whitfield et al. | 606/144 |
| 5,490,858 A | | 2/1996 | Shuter | |
| 5,531,695 A | * | 7/1996 | Swisher | 604/111 |
| 5,566,822 A | | 10/1996 | Scanlon | |
| 5,603,718 A | * | 2/1997 | Xu | 606/145 |
| 5,620,460 A | * | 4/1997 | Smith | 606/205 |
| 5,730,747 A | * | 3/1998 | Ek et al. | 606/148 |
| 5,752,957 A | * | 5/1998 | Ralph et al. | 606/266 |
| 5,769,223 A | | 6/1998 | Marsh | |
| 5,799,788 A | | 9/1998 | Webb | |
| 5,817,094 A | * | 10/1998 | Errico et al. | 606/264 |
| 5,935,149 A | * | 8/1999 | Ek | 606/232 |

(Continued)

*Primary Examiner*—(Jackie) Tan-Uyen T Ho
*Assistant Examiner*—Jing Ou
(74) *Attorney, Agent, or Firm*—Anthony D. Pellegrini

(57) ABSTRACT

An improved suture needle retention device suitably adapted to be removably attached to the end of a surgical instrument for convenient placement proximate to the surgical field yet out of the way of the surgeon, said device having a needle pervious retention member to accept the sharp end of a suture needle, with said retention member encased by a needle impervious protective sheathing to prevent inadvertent pass-through of the suture needle.

6 Claims, 7 Drawing Sheets

U.S. PATENT DOCUMENTS

| | | | |
|---|---|---|---|
| 5,947,982 A * | 9/1999 | Duran | 606/139 |
| 5,957,937 A * | 9/1999 | Yoon | 606/147 |
| 6,059,829 A * | 5/2000 | Schlapfer et al. | 623/17.16 |
| 6,063,090 A * | 5/2000 | Schlapfer | 606/270 |
| 6,380,483 B1 * | 4/2002 | Blake | 174/668 |
| RE37,908 E * | 11/2002 | Kinsey | 600/577 |
| 2002/0063074 A1 | 5/2002 | Simm et al. | |
| 2002/0077602 A1 * | 6/2002 | Hsu | 604/240 |
| 2003/0097098 A1 * | 5/2003 | Lavi et al. | 604/263 |
| 2003/0100881 A1 * | 5/2003 | Hwang | 604/403 |
| 2005/0033324 A1 * | 2/2005 | Phan | 606/148 |
| 2005/0096695 A1 * | 5/2005 | Olich | 606/213 |
| 2005/0222612 A1 * | 10/2005 | Vries et al. | 606/206 |
| 2007/0119739 A1 * | 5/2007 | Clegg et al. | 206/365 |

* cited by examiner

SUTURE NEEDLE RETENTION DEVICE

BACKGROUND OF THE INVENTION

1. Technical Field

The invention relates generally to the field of surgical instruments and accessories. More specifically, the invention is directed to an improved suture needle retention device to be used during the suturing procedure to provide a temporary safe location for a suture needle while the surgeon ties off the suture or performs other activities.

2. Description of Prior Art

Injuries resulting from accidental contact with a sharp medical instrument are fairly common in surgical procedures. These so-called "sharps" injuries present a high risk to surgeons, physicians assistants, nurses, and other medical personnel in light of the prevalence of infectious blood-borne diseases, such as HIV and hepatitis B. The danger is so serious that OSHA has promulgated regulations directed to the safe handling of sharps.

A common source of sharps injuries are suture needles. It is estimated that twenty percent of all sharps injuries are from suture needles, representing more than 100,000 injuries each year in the United States. The Center for Disease Control reports that approximately twenty percent of all cases of HIV infection from needle sticks arise specifically from suture needles.

Suture needles are typically curved needles attached to the end of a length of suture material. A surgical instrument known as a needle driver is used to hold the end of the suture needle closest to the suture, and the surgeon, manipulating the needle driver, maneuvers the sharp end of the suture needle into and through skin or other tissue, pulling the suture material along with it. The surgeon then ties off the suture with a secure knot, cutting the excess suture material. The process is repeated for as many sutures are needed. During the tying and cutting phase of the procedure the suture needle is not used by the surgeon. It is typically held between the surgeon's fingers, left to hang from the excess suture material, or set down upon the surgical field, or otherwise placed out of the way. As such it becomes a danger to all persons in close proximity to it.

A suture needle retention device lessens the danger of an accidental sharps injury from a suture needle during the tying and cutting phase of suturing by providing a secure place to embed the sharp end of the suture needle. However, the suture needle retention devices known in the art are deficient in many respects. Some are designed to be simply placed on a flat surface, where they may be inconvenient to the surgeon or in danger of being knocked to the floor. Others are designed to be worn on the surgeon's wrist or held in the surgeon's hand. These configurations present the danger of a surgeon attempting to place the suture needle into the device but then missing and sticking him- or herself. This is clearly unacceptable. Other devices are designed to be affixed to a surgical instrument. This is an improvement, as it places the device in a useful location, but attachment means comprising adhesives tend to leave a residue upon the instrument, making cleanup and/or sterilization more difficult, and attachment means comprising magnets tend not to hold the devices securely enough.

Following are examples of surgical needle retention devices known in the art. Cramer, U.S. Pat. No. 4,380,292 (Apr. 19, 1983), "Parenteral Needle Receptacle", discloses a foam block needle park encased in a plastic container having a top aperture. Needles are passed through the aperture into the foam block. The container retains the foam block and has a means for attaching the device to a surface, such as by adhesive tape or a magnet. The container comes apart to permit disposal of the needle-filled foam block and insertion of a fresh foam block. It is intended primarily as a disposal device for needles, as opposed to device for temporarily securing a suture needle during the suturing procedure. The attachment means are inferior, as the use of an adhesive leaves a residue behind when the device is removed, making it difficult to sterilize the surface onto which the device was attached. The use of magnetic attachment means is also inferior, as the device is easily dislodged even during ordinary use. Moreover, the device is not intended to be attached to a surgical instrument by any attachment means.

Swor, U.S. Pat. No. 4,969,893 (Nov. 13, 1990), "Disposable Suture Cutter and Needle Holder", discloses a suture cutting device having a foam needle park to temporarily receive the suture needle. It may be laid upon a flat surface or attached to a surface, such as a surgical drape, or to the surgeon's hand or wrist. It is not intended to be attached to a surgical instrument.

Shuter, U.S. Pat. No. 5,490,858 (Feb. 13, 1996), "Method and Apparatus for Handling Suturing Needles", discloses, though does not claim, a needle retention device comprised of a needle pervious retaining material with a needle impervious cap provided over a portion of the retaining material to prevent penetration of the needle completely through the retaining material. The Shuter device is intended to be held by the hand of the user. Shuter suggests the device can be attached to an instrument by hook and loop fasteners or magnetic means, but discloses no integrated means for securely attaching the device to a surgical instrument.

The above-cited prior art is easily distinguished from the present invention. The present invention is directed to a suture needle retention device which integrates easily and securely with a surgical instrument, such as a forceps, typically used by the surgeon to hold tissue during the suturing procedure. Attachment of the present invention to the surgical instrument keeps the device out of the way when not in use but allows it to be immediately accessible when needed. More importantly, it directs the temporary placement of suture needles away from the surgeon's hand. Its novel attachment component allows for simple interchangeability between instruments, if needed, and easy removal and disposal without compromising the surgical instrument. It is not, however, a permanent needle disposal device nor a device intended to store, cut, or retain sutures or multiple needles.

These and other features of the present invention, described below, disclose a novel and useful invention.

It is an objective of the present invention to provide an improved suture needle retention device to receive and temporarily hold a suture needle during a suturing procedure to keep the suture needle safely out of the surgeon's way while the surgeon completes tying the suture or performs some other task.

It is a further objective to provide an improved suture needle retention device that increases the safety to the surgeon by locating the device away from the surgeon's hand during use.

It is a further objective to provide an improved suture needle retention device that increases the safety to the surgeon by directing the path of the suture needle away from the surgeon's hand when used to retain the suture needle.

It is a further objective to provide an improved suture needle retention device that integrates easily and securely with a surgical instrument, thereby keeping the device out of the way when not in use but immediately accessible when needed.

It is a further objective to provide an improved suture needle retention device that is removably attachable to a surgical instrument by means providing secure attachment thereto and easy removal therefrom.

It is a further objective to provide an improved suture needle retention device that comprises an attachment means which does not compromise the surgical instrument to which it is attached during use.

It is a further objective to provide an improved suture needle retention device that allows for simple interchangeability between instruments, if needed.

It is yet a further objective to provide an improved suture needle retention device that is simple and cost effective to manufacture.

Other objectives of the present invention will be readily apparent from the description that follows.

SUMMARY OF THE INVENTION

The invention comprises an improved suture needle retention device suitably adapted to be removably attached to the end of a surgical instrument held in the nondominant hand of the surgeon. The suture needle retention device accepts the sharp end of a suture needle and holds it securely, until such time as a sufficient forced is applied to extract the suture needle from the device.

The suture needle retention device is comprised of a retention member, a protective sheathing, and an attachment component. The retention member is constructed of a needle pervious material, such as closed cell foam. The protective sheathing is constructed of a needle impervious material, such as a rigid plastic, and encloses most of the retention member, leaving a portion of the retention member exposed so as to receive the sharp end of the suture needle. A suture needle inserted too deeply into the retention member will strike the protective sheathing and be prevented from penetrating through the protective sheathing to the exterior of the device. The protective sheathing may also comprise structures within its interior to better secure the retention member within the protective sheathing. The attachment component is integrated with the protective sheathing and comprises one or more slots formed into the end of the protective sheathing opposite the exposed retention member. These slots are suitably adapted to accommodate the end of a surgical instrument. The attachment component may comprise additional structures to more firmly attach the device to the surgical instrument, such as a flexible flap that frictionally engages with the end of the surgical instrument.

The above configuration aligns the suture needle retention device substantially perpendicular to the end of the surgical instrument, such that movement of the suture needle towards the device is not towards the surgeon's hand holding the instrument.

The attachment component allows the suture needle retention device to be easily placed onto and taken off the end of the surgical instrument. It can be quickly swapped onto different instruments if needed. If it becomes unusable during a suturing procedure it can be easily removed and disposed of and a replacement placed onto the surgical instrument.

Other features and advantages of the invention are described below

DETAILED DESCRIPTION OF THE INVENTION

Figure 1:
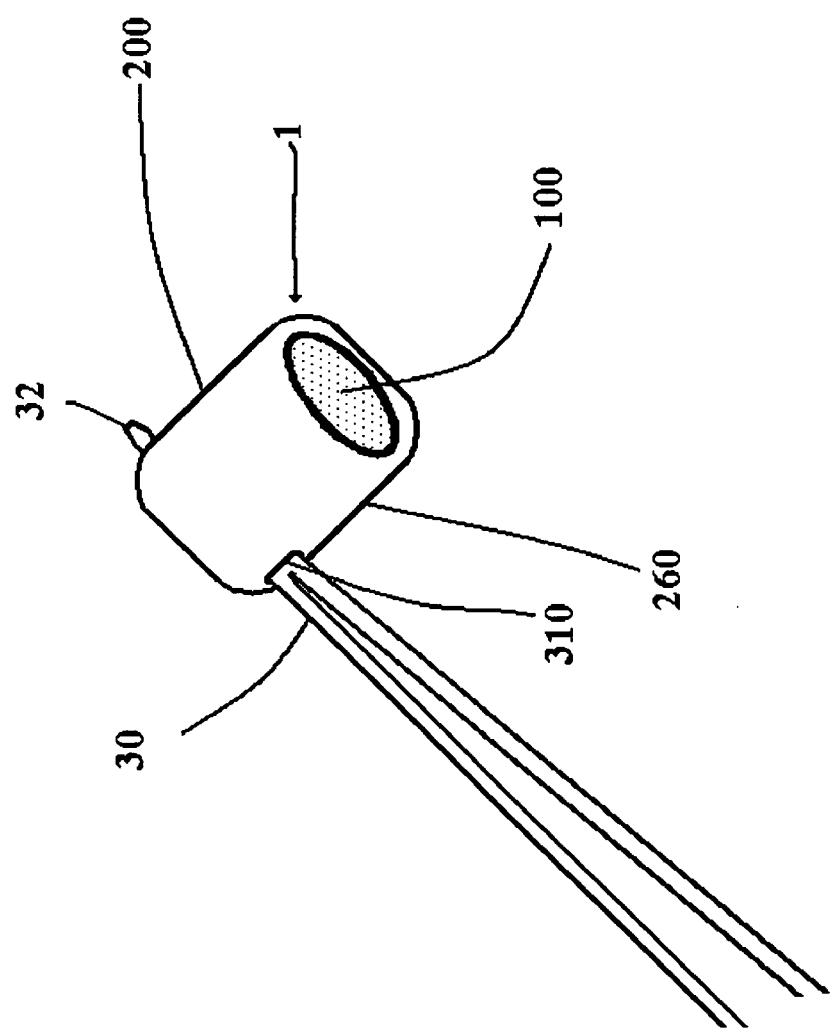
FIG. 1 is a perspective view of the present invention depicting the invention attached to the end of a forceps.
Figure 6:
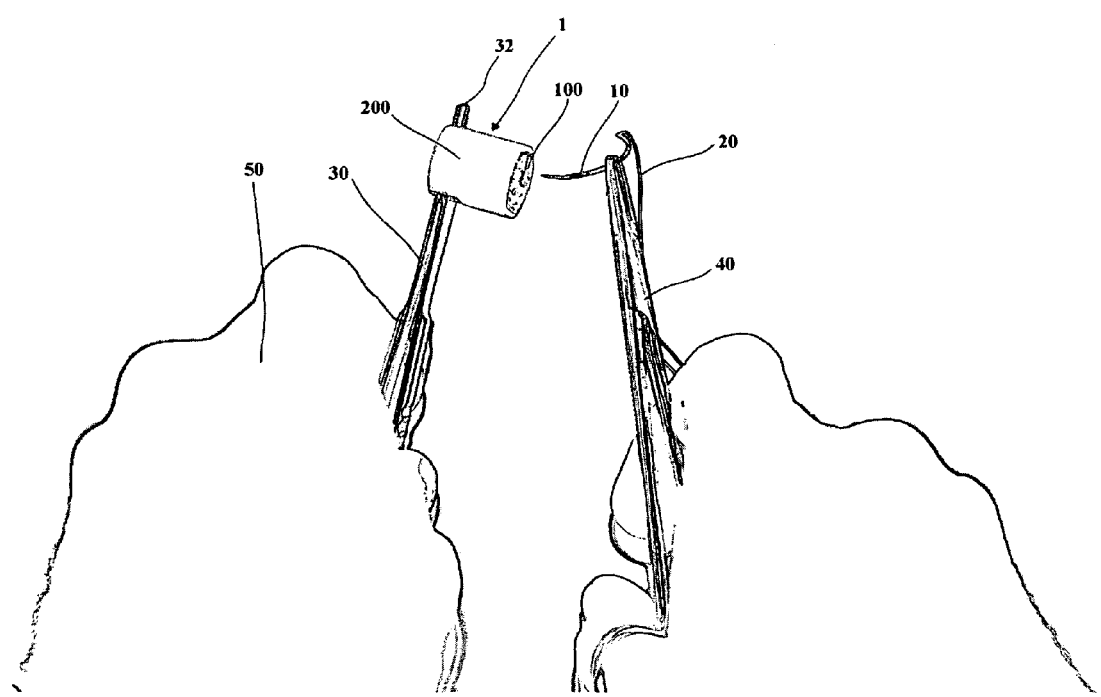
FIG. 6 is a perspective view of the present invention being used by a surgeon, depicting the surgeon directing the suture needle towards the retention member of the device.
Figure 7:
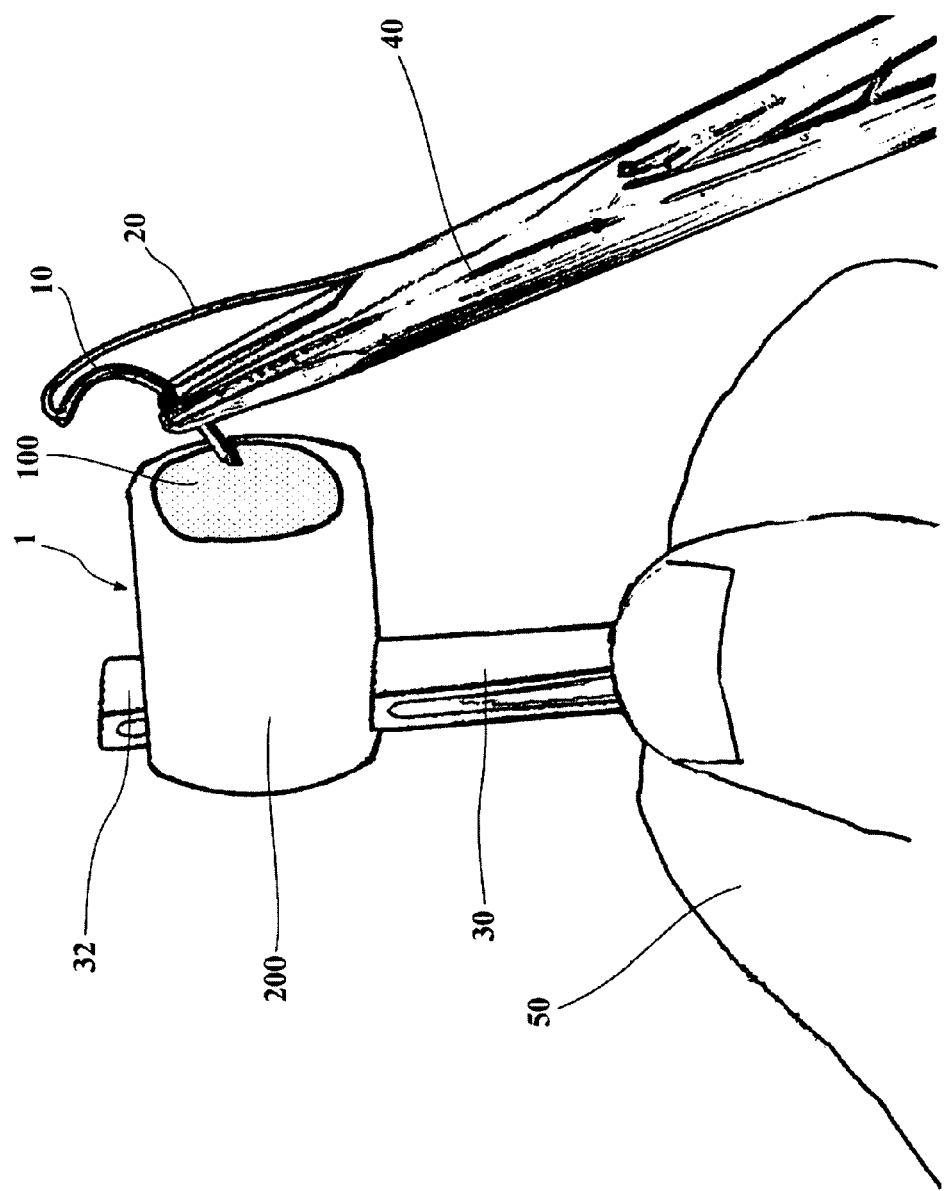
FIG. 7 is a perspective view of the present invention being used by a surgeon, depicting the suture needle embedded in the retention member of the device.

The present invention is an improved suture needle retention device 1 to be used by a surgeon during a suturing procedure. See FIG. 1. The device 1 is suitably adapted to be removably attached to the end 32 of a surgical instrument 30, such as a forceps, held in the nondominant hand 50 of the surgeon. See FIG. 6. The surgeon, holding a suture needle 10 with a needle driver 40 held in the dominant hand of the surgeon, directs the sharp end of the suture needle 10 into the device 1, such that the sharp end of the suture needle 10 becomes embedded within the device 1 so that the device 1 holds the suture needle 10 securely and safely while the surgeon ties off and cuts the suture 20 or performs some other function. See FIG. 7. When the surgeon again requires use of the suture needle 10, it is withdrawn from the device 1 by the surgeon and used to continue with the suturing procedure.

The suture needle retention device 1 is comprised of a retention member 100, a protective sheathing 200, and an attachment component 300. The retention member 100 is contained substantially within the protective sheathing 200, and the attachment component 300 is formed into and integrated with the protective sheathing 200.

The retention member 100 is needle pervious. When used as intended, the retention member 100 is pierced by a suture needle 10 such that at least the sharp end of the suture needle 10 becomes embedded within the retention member 100, with the remaining portion of the suture needle 10 being exposed exterior to the retention member 100. Placed as such, the suture needle 10 is retained securely by the retention member 100 and the potentially dangerous sharp end of the suture needle 10 is not exposed. The retention member 100 is also suitably adapted to release the suture needle 10 embedded therein when a sufficient extraction force is applied to the suture needle 10. The retention member 100 is preferably constructed of a resilient, deformable material, to allow it to be placed within the protective sheathing 200 of the device 1. The retention member 100 should be constructed of a material having negligible friability, so that the retention member 100 resists shedding portions of its material upon being pierced by a suture needle 10. It should also be sufficiently durable to withstand multiple insertions and extractions of a suture needle 10. The retention member 100 may be constructed of any material having the foregoing characteristics, with the preferred material being a closed cell foam. In the most preferred embodiment, the retention member 100 is constructed of low density polyethylene #2 medical grade closed cell foam.

The protective sheathing 200 is constructed of a needle impervious material. The protective sheathing 200 should be substantially rigid and light weight. It may be constructed of any suitable material, with the preferred material being a rigid plastic. In the most preferred embodiment, the protective sheathing is constructed of ABS plastic. This allows for cost effective manufacture using well known injection molding techniques.

Figure 2:
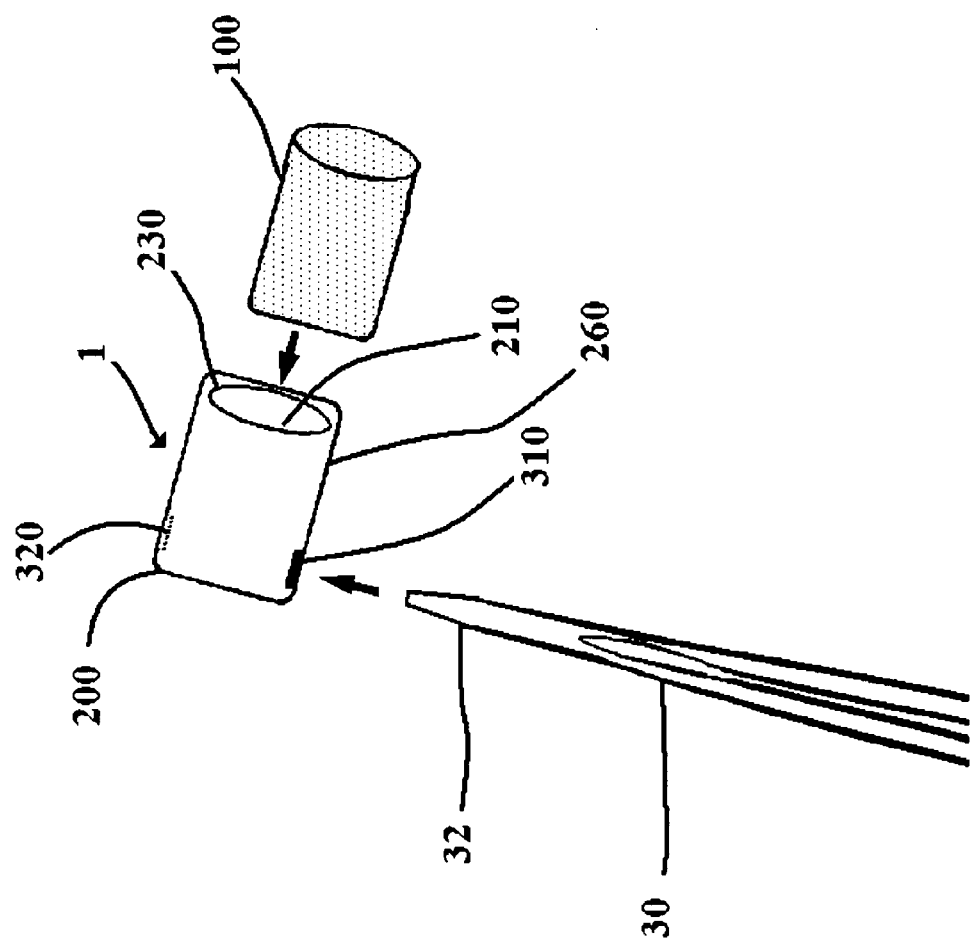
FIG. 2 is an exploded view of the present invention depicted in FIG. 1.
Figure 3:
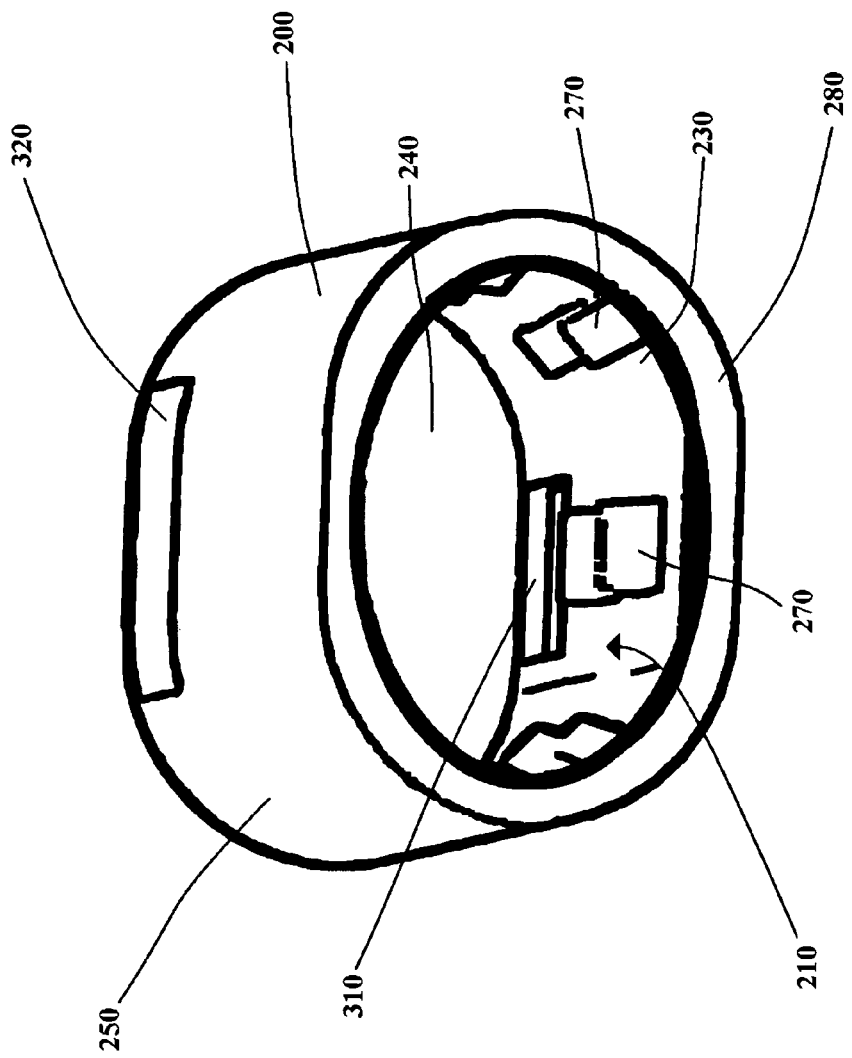
FIG. 3 is a perspective front view of the protective sheathing of the present invention.

The protective sheathing 200 must be suitably adapted to enclose most of the retention member 100, leaving at least a portion of the retention member 100 exposed so as to receive the sharp end of the suture needle 10. The protective sheathing 200 is substantially hollow and has an interior 210, and has an open end 230 providing access into the interior 210. See FIG. 3. Opposite the open end 230, the protective sheathing has a closed end 240. At least a portion of the retention member 100 is inserted into the interior 210 of the protective sheathing 200. See FIG. 2. In the preferred embodiment the entire retention member 100 is enclosed by the protective sheathing 200, with one surface of the retention member 100 exposed through the open end 230 of the protective sheathing 200. See FIG. 1. To use the device 1, a suture needle 10 is inserted into the retention member 100 through the open end 230 of the protective sheathing 200. See FIGS. 6 and 7. Even if the suture needle 10 is attempted to be inserted too deeply into the retention member 100, it cannot pass through the protective sheathing 200 and thus the sharp end of the suture needle 10 is prevented from penetrating through to the exterior of the device 1.

The protective sheathing 200 may be of any shape suitable to enclose the retention member 100 while leaving at least a portion of the retention member 100 exposed. It can be of any size as well, though in practical application the protective sheathing 200 should be between one half inch to two inches long from its open end 230 to its closed end 240, and between one half inch and one inch across its open end 230. The retention member 100 should have a shape conforming substantially to the shape of the interior 210 of the protective sheathing 200, to provide for a snug fit within the protective sheathing 200. As such, the retention member 100 is frictionally secured within the protective sheathing 200. In one embodiment the protective sheathing 200 is semi-spherical in shape. In another embodiment the protective sheathing 200 is cylindrical. In the preferred embodiment the protective sheathing 200 is a flattened cylinder. See FIG. 3. In this embodiment the protective sheathing 200 has a top side 250 and a bottom side 260, and the closed end 240 of the protective sheathing 200 is substantially planar and oriented substantially parallel to the plane of the open end 230 of the protective sheathing 200.

Figure 4:
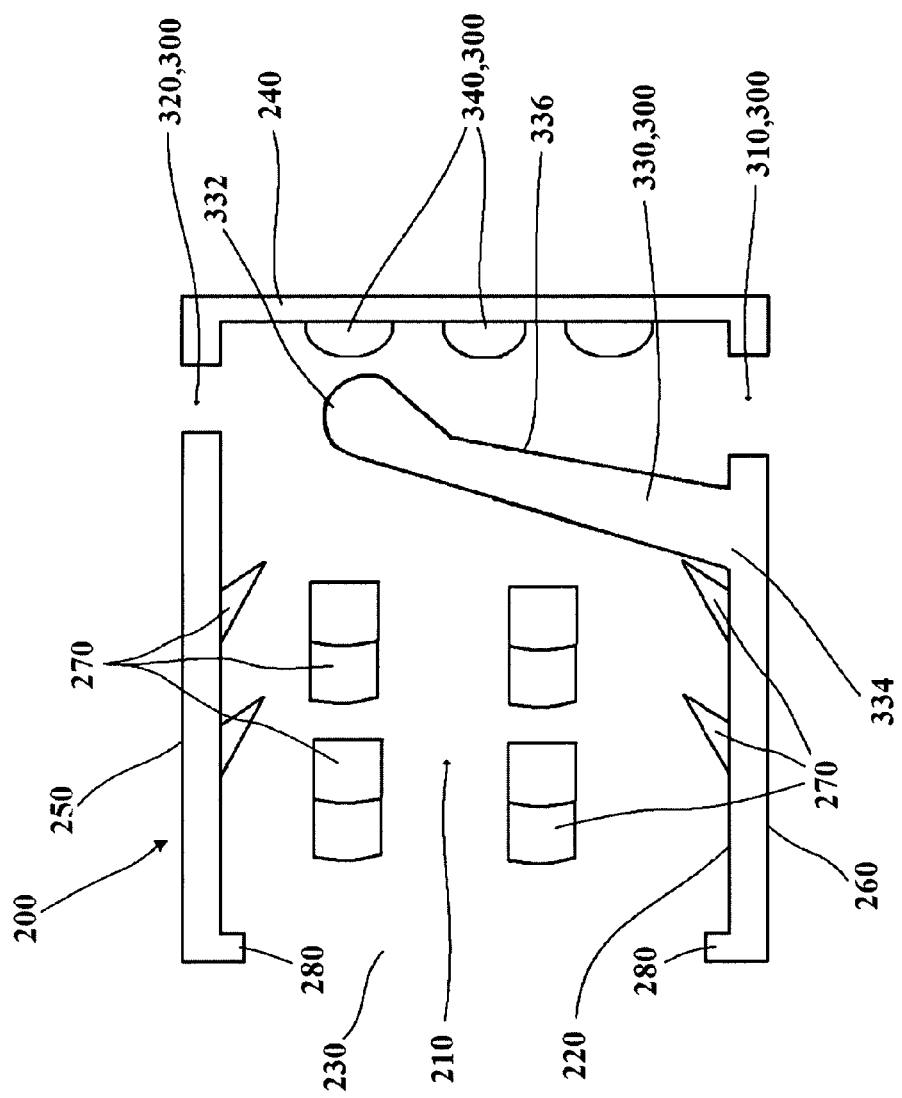
FIG. 4 is a cut-away side view of the protective sheathing of the present invention depicting the integrated attachment component.

The protective sheathing 200 may also comprise structures within its interior 210 to better secure the retention member 100 within the protective sheathing 200. See FIG. 4. In one embodiment, the protective sheathing 200 comprises a plurality of engagement barbs 270. The engagement barbs 270 are located within the interior 210 of the protective sheathing 200 on the interior surface 220 of the protective sheathing 200. Each engagement barb 270 protrudes into the interior 210 of the protective sheathing 200 and is oriented towards the closed end 240 of the protective sheathing 200. When the retention member 100 is inserted into the interior 210 of the protective sheathing 200, the retention member 100 deforms around the engagement barbs 270 and the rearward orientation of the engagement barbs 270 prevents the retention member 100 from slipping out of the open end 230 of the protective sheathing 200.

In another embodiment, the protective sheathing 200 comprises a retention lip 280. The retention lip 280 is located circumferentially about the open end 230 of the protective sheathing 200 and extends into the open end 230. As such, the retention lip 280 assists in retaining the retention member 100 within the interior 210 of the protective sheathing 200. In yet another embodiment both the engagement barbs 270 and the retention lip 280 are present. In yet a further embodiment at least a portion of the interior surface 220 of the protective sheathing 200 is textured, providing enhanced frictional means for retaining the retention member 100 within the protective sheathing 200. The above described structures may be formed into the protective sheathing 200 during manufacture, for example by using injection molding techniques, resulting in a monolithic component with integrated interior structures.

The above configurations of the protective sheathing 200 are suitably adapted to allow for easy insertion of at least a portion of the retention member 100 into the interior 210 of the protective sheathing 200. Final assembly of the device 1 is simplified by merely directing the retention member 100 into the interior 210 of the protective sheathing 200 with sufficient force to cause the retention member 100 to deform past and around the various structures present. No adhesive is needed to retain the retention member 100 within the protective sheathing 200. Moreover, if desired, the retention member 100 may be removed from the protective sheathing 200, for example by grasping it with tweezers and then extracting it through the open end 230 of the protective sheathing 200, thereafter to be replaced by a new retention member 100.

The attachment component 300 of the device 1 is integrated with the protective sheathing 200. The attachment component 300 is suitably adapted to permit the device 1 to be removably attached to a surgical instrument 30 without the use of adhesives or straps. It secures the device 1 to the surgical instrument 30 sufficiently to prevent accidental detachment during use as well as aligns the device 1 with the surgical instrument 30 such that during use the suture needle 10 is never directed towards the surgeon's hand 50.

The attachment component 300 comprises at least one slot formed into the protective sheathing 200. The slot is located proximate to the closed end 240 of the protective sheathing 200, formed into the bottom side 260 of the protective sheathing 200, and oriented such that its length is substantially parallel to the plane of the closed end 240 of the protective sheathing 200. The slot is suitably adapted to accommodate an end 32 of a surgical instrument 30, whereby the end 32 of the surgical instrument 30 may be inserted into and through the slot into the interior 210 of the protective sheathing 200. The device 1 is frictionally secured to the surgical instrument 30 by the sides of the slot surrounding the instrument 30 and the end 32 of the instrument 30 being pressed between the closed end 240 of the protective sheathing 200 and the rear portion of the retention member 100.

In the preferred embodiment, the attachment component 300 comprises a bottom slot 310 and a top slot 320. The bottom slot 310 is located proximate to the closed end 240 of the protective sheathing 200, formed into the bottom side 260 of the protective sheathing 200, and oriented such that its length is substantially parallel to the plane of the closed end 240 of the protective sheathing 200. The top slot 320 is formed into the top side 250 of the protective sheathing 200 proximate to the closed end 240 of the protective sheathing 200, and is oriented substantially in alignment with the bottom slot 310. The width of the top slot 320 is less than the width of the bottom slot 310. See FIG. 4. The bottom slot 310 and the top slot 320 are suitably adapted to accommodate the end 32 of a surgical instrument 30, whereby the end 32 of the surgical instrument 30 may be inserted into and through the bottom slot 310 into the interior 210 of the protective sheathing 200 and then into and through the top slot 320 from the interior 210 of the protective sheathing 200 and out of the protective sheathing 200. This results in at least a portion of the surgical instrument 30 being contained within the interior 210 of the protective sheathing 200, the end 32 of the instrument 30 protruding from the top slot 320, and the remainder of the instrument 30 protruding from the bottom slot 310. Because the width of the top slot 320 is less than the width of the bottom slot 310, and the end 32 of the surgical instrument 30 is typically tapered, the end 32 of the surgical instrument 30 can pass only a short way through the top slot 320 before becoming wedged therein. The device 1 is therefore secured to the surgical instrument 30 by the sides of the bottom and top slots 310,320 surrounding the instrument 30. In certain configurations the portion of the instrument 30 contained within the interior 210 of the protective sheathing 200 is also pressed between the closed end 240 of the protective sheathing 200 and the rear portion of the retention member 100. In one embodiment the interior surface 220 of the closed end 240 of the protective sheathing 200 is textured, enhancing the ability of the device 1 to be frictionally secured to the instrument 30.

With the bottom and top slots 310,320 of the attachment component 300 formed into the protective sheathing 200 as described above, the device 1 attaches to the surgical instrument 30 in a substantially perpendicular orientation. That is, the longitudinal axis of the device 1, running through the open and closed ends 230,240 of the protective sheathing 200, is substantially perpendicular to the longitudinal axis of the surgical instrument 30. So oriented, the exposed portion of the retention member 100 lies in a plane substantially parallel to the surgical instrument 30. See FIGS. 6 and 7. Thus, when a surgeon directs the suture needle 10 towards the device 1, the suture needle 10 does not move towards the hand 50 holding the instrument 30. This is in contrast to other devices known in the art, such as those worn on a wrist band or held in the surgeon's hand. In those configurations the suture needle 10 is directed towards the surgeon's hand 50; if the suture needle 10 misses the device, it is likely to strike the hand 50, causing injury. The present invention avoids this undesirable risk. If the surgeon misses the retention member 100, the suture needle 10 is likely to strike either the surgical instrument 30 or nothing at all. This configuration also enhances the security of the attachment of the device 1 to the instrument 30. This is because the forces necessary to insert the suture needle 10 into the retention member 100 and to extract the suture needle 10 from the retention member 100 are applied perpendicular to the directions of force needed to attach or detach the device 1 to the instrument 30, so that normal use of the device 1 does not tend to loosen the device 1 from the instrument 30.

Figure 5:
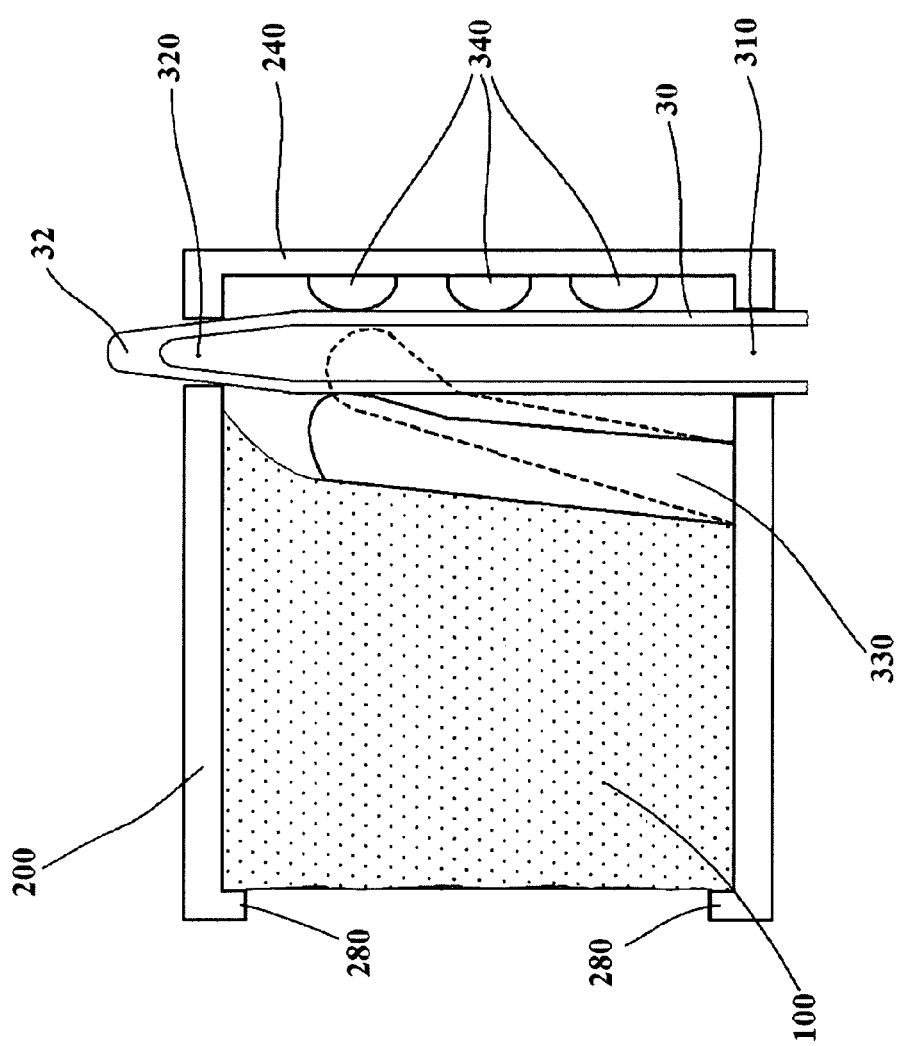
FIG. 5 is a cut-away side view of the protective sheathing of the present invention depicting the retention flap being displaced against the retention member by the surgical instrument, resulting in the surgical instrument being held securely between the retention flap, the retention ridges, and the edges of the top and bottom slots of the attachment component.

The attachment component 300 may comprise additional structures to more firmly attach the device 1 to the surgical instrument 30. One such structure is a flexible retention flap 330. The retention flap 330 is substantially planar and has a top edge 332, a connection end 334 located opposite the top edge 332, and a face 336. The retention flap 330 is located within the interior 210 of the protective sheathing 200 proximate to the bottom slot 310 and between the bottom slot 310 and the open end 230 of the protective sheathing 200, such that the retention flap 330 is located between the retention member 100 and the bottom slot 310. The retention flap 330 is attached to the interior surface 220 of the bottom side 260 of the protective sheathing 200 at its connection end 334, with the face 336 of the retention flap 330 oriented towards and substantially parallel to the closed end 240 of the protective sheathing 200. The face 336 of the retention flap 330 may be textured. The retention flap 330 is angled towards the closed end 240 of the protective sheathing 200 such that the top edge 332 and at least a portion of the face 336 of the retention flap 330 extend over at least a portion of the bottom slot 310. So configured, the retention flap 330 is suitably adapted to flex and to be displaced in a direction away from the closed end 240 of the protective sheathing 200. When a surgical instrument 30 is inserted into the bottom slot 310 and out through the top slot 320, as described above, at least a portion of the instrument 30 contained within the interior 210 of the protective sheathing 200 presses against at least a portion of the face 336 of the retention flap 330 and displaces the retention flap 300 away from the closed end 240 of the protective sheathing 200 and against the retention member 100. See FIG. 5. The retention flap 330 in turn presses back against the portion of the instrument 30 contained within the interior 210 of the protective sheathing 200 as a result of its flexing and the counter force of the retention member 100 pressing the retention flap 330 back against the instrument 30. In this manner the device 1 is even more securely attached to the instrument 30.

The attachment component 300 may also comprise at least one retention ridge 340. Each retention ridge 340 is located on the interior surface 220 of the closed end 240 of the protective sheathing 200. Each retention ridge 340 is oriented substantially horizontally and extends into the interior 210 of the protective sheathing 200 from the interior surface 206 of the closed end 240 of the protective sheathing 200 such that at least a portion of the retention ridge 340 is aligned over at least a portion of the bottom slot 310. See FIGS. 4 and 5. The retention ridges 340 provide a greater surface area against which the surgical instrument 30 is pressed when it is inserted through the bottom and top slots 310,320.

The preferred embodiment uses both the retention ridges 340 and the retention flap 330, located on either side of the instrument 30, respectively, to maximize the points of contact between the instrument 30 and the device 1, thereby enhancing the security of the attachment. This provides an improvement over the prior art which might attach a suture needle retention device using a magnet or a strap. A magnet small enough to be used with a practically sized device will not have sufficient holding power to retain the device securely to the instrument 30, but rather the device will tend to slide along the instrument 30 and possibly be pulled off the instrument 30 when extracting the suture needle 10 therefrom. Straps are not only awkward to use but may permit a device to rotate about the instrument 30, taking the device out of its desired alignment. Adhesives may hold a device more securely than a magnet or straps, but then the device cannot be easily removed from the instrument 30. Also, once the device is removed from the instrument 30, a residue of the adhesive will remain behind, making the instrument 30 harder to clean and sterilize. The present invention overcomes all of these deficiencies by providing a secure attachment that prevents the device 1 from moving in relation to the instrument 30 when attached thereto, but also is easily removed when no longer needed. This is especially important if the surgeon needs to use different instruments during the procedure; the device 1 can be easily swapped from one instrument to another.

The device 1 configured in its most preferred embodiment, with the protective sheathing 200 comprising a plurality of engagement barbs 270, a retention lip 280, a retention flap 330, and one or more retention ridges 340, may be manufactured with the protective sheathing 200 and all said component structures being formed as a monolithic unit in a single manufacturing step, such as injection molding. Assembly of the device 1 is easily completed by simply inserting the retention member 100 into the protective sheathing 200 through the open end 230. As such, the present invention represents an improvement over the more complicated devices represented by the prior art with regard to cost and ease of manufacture.

Other embodiments not specifically set forth herein are also within the scope of the following claims.

I claim:

1. A suture needle retention device comprising
   a retention member,
      said retention member being needle pervious,
      said retention member suitably adapted to be pierced by a suture needle such that a portion of the suture needle is embedded within said retention member,
      said retention member suitably adapted to retain an embedded suture needle securely, and
      said retention member suitably adapted to release an embedded suture needle when a sufficient extraction force is applied to the suture needle;
   a protective sheathing,
      said protective sheathing being needle impervious,
      said protective sheathing being substantially hollow and having an interior and an interior surface,
      said protective sheathing having an open end providing access into the interior,
      said protective sheathing having a closed end that is substantially planar and located substantially opposite the open end,
      said protective sheathing having a top side and a bottom side, and
      said protective sheathing suitably adapted to contain at least a portion of the retention member within its interior while exposing another portion of the retention member; and
   an attachment component,
      said attachment component comprising
         a bottom slot,
            said bottom slot formed into the bottom side of the protective sheathing proximate to the closed end of the protective sheathing and providing access into the interior of the protective sheathing,
            said bottom slot having a width and a length,
               said length of said bottom slot oriented substantially parallel with the closed end of the protective sheathing, and
            said bottom slot being suitably adapted to accommodate an end of the surgical instrument such that the end of the surgical instrument is inserted through the bottom slot into the interior of the protective sheathing,
         a top slot,
            said top slot formed into the top side of the protective sheathing proximate to the closed end of the protective sheathing and providing access into the interior of the protective sheathing,
            said top slot having a width and a length, said width of the top slot being less than the width of the bottom slot,
            said top slot oriented substantially in alignment with the bottom slot, and
            said top slot being suitably adapted to accommodate the end of the surgical instrument such that the end of the surgical instrument is inserted through the top slot from the interior of the protective sheathing, and
      a retention flap,
         said retention flap being substantially planar and having a top edge, a connection end opposite said top edge, and a face,
         said retention flap located within the interior of the protective sheathing proximate to the bottom slot and between the bottom slot and the open end of the protective sheathing,
         said retention flap being flexibly attached to the interior surface of the protective sheathing at its connection end, with the face of the retention flap oriented towards and substantially parallel to the closed end of the protective sheathing,
         said retention flap extending into the interior of the protective sheathing from the interior surface of the protective sheathing and oriented at an angle towards the closed end of the protective sheathing, such that the top edge and at least a portion of the face extend over at least a portion of the bottom slot,
         said retention flap being suitably adapted to press at least a portion of its face against the surgical instrument and to be displaced towards the open end of the protective sheathing when the surgical instrument is inserted through the bottom slot and top slot, and
      said attachment component is suitably adapted to removably attach the suture needle retention device to a surgical instrument without the use of adhesives;
      whereby the attachment component is integrated with the protective sheathing, and at least a portion of the retention member is contained within the interior of the protective sheathing and the surgical instrument protrudes through the bottom and top slots of the protective sheathing with the end of the surgical instrument protruding from the top slot.

2. The suture needle retention device of claim 1 wherein the face of the retention flap is textured.

3. The suture needle retention device of claim 1 wherein the interior surface of the closed end of the protective sheathing is textured.

4. The suture needle retention device of claim 1 wherein the attachment component further comprises at least one retention ridge,
   each said retention ridge located on the interior surface of the closed end of the protective sheathing,
   each said retention ridge being oriented substantially horizontally, and
   each said retention ridge extending into the interior of the protective sheathing from the interior surface of the closed end of the protective sheathing such that at least a portion of said retention ridge is aligned over at least a portion of the bottom slot.

5. A suture needle retention device comprising
   a retention member,
      said retention member being needle pervious,
      said retention member suitably adapted to be pierced by a suture needle such that a portion of the suture needle is embedded within said retention member,
      said retention member suitably adapted to retain an embedded suture needle securely, and
      said retention member suitably adapted to release an embedded suture needle when a sufficient extraction force is applied to the suture needle;
   a protective sheathing, said protective sheathing being needle impervious,
said protective sheathing being substantially hollow and having an interior and an interior surface,
said protective sheathing having an open end providing access into the interior,
said protective sheathing having a closed end that is substantially planar and located substantially opposite the open end,
said protective sheathing having a top side and a bottom side, and
said protective sheathing suitably adapted to contain at least a portion of the retention member within its interior while exposing another portion of the retention member; and an attachment component,
said attachment component comprising
a bottom slot,
said bottom slot formed into the bottom side of the protective sheathing proximate to the closed end of the protective sheathing and providing access into the interior of the protective sheathing,
said bottom slot having a width and a length,
said length of said bottom slot oriented substantially parallel with the closed end of the protective sheathing, and
said bottom slot being suitably adapted to accommodate an end of the surgical instrument such that the end of the surgical instrument is inserted through the bottom slot into the interior of the protective sheathing,
a top slot,
said top slot formed into the top side of the protective sheathing proximate to the closed end of the protective sheathing and providing access into the interior of the protective sheathing,
said top slot having a width and a length, said width of the top slot being less than the width of the bottom slot,
said top slot oriented substantially in alignment with the bottom slot, and
said top slot being suitably adapted to accommodate the end of the surgical instrument such that the end of the surgical instrument is inserted through the top slot from the interior of the protective sheathing, and
at least one retention ridge,
each said retention ridge located on the interior surface of the closed end of the protective sheathing,
each said retention ridge being oriented substantially horizontally, and
each said retention ridge extending into the interior of the protective sheathing from the interior surface of the closed end of the protective sheathing such that at least a portion of said retention ridge is aligned over at least a portion of the bottom slot,
said attachment component suitably adapted to removably attach the suture needle retention device to a surgical instrument without the use of adhesives;
whereby the attachment component is integrated with the protective sheathing, and at least a portion of the retention member is contained within the interior of the protective sheathing and the surgical instrument protrudes through the bottom and top slots of the protective sheathing with the end of the surgical instrument protruding from the top slot.

6. A suture needle retention device comprising
a retention member,
said retention member being needle pervious, being comprised of a resilient closed-cell foam having negligible friability,
said retention member suitably adapted to be pierced by a suture needle such that a portion of said suture needle is embedded within a portion of said retention member,
said retention member suitably adapted to retain said embedded suture needle securely, and
said retention member suitably adapted to release said embedded suture needle when a sufficient extraction force is applied to said suture needle;
a protective sheathing,
said protective sheathing being needle impervious,
said protective sheathing being substantially hollow and having an interior and an interior surface,
said protective sheathing having an open end providing access into the interior,
said protective sheathing having a closed end opposite the open end, said closed end being substantially planar and the interior surface of said closed end being textured,
said protective sheathing having a top side and a bottom side,
said protective sheathing containing the retention member within the interior of the protective sheathing,
said protective sheathing further comprising a plurality of engagement barbs,
said engagement barbs located within the interior of the protective sheathing on the interior surface of the protective sheathing,
with each said engagement barb protruding into the interior of the protective sheathing from the interior surface of the protective sheathing and oriented towards the closed end of the protective sheathing, and
said protective sheathing further comprising a retention lip,
said retention lip located circumferentially about the open end of the protective sheathing; and
an attachment component, said attachment component comprising
a bottom slot,
said bottom slot formed into the bottom side of the protective sheathing proximate to the closed end of the protective sheathing and providing access into the interior of the protective sheathing,
said bottom slot having a width and a length,
said length of said bottom slot oriented substantially parallel with the closed end of the protective sheathing,
said bottom slot being suitably adapted to accommodate an end of a surgical instrument such that the end of the surgical instrument is inserted through the bottom slot into the interior of the protective sheathing,
a top slot,
said top slot formed into the top side of the protective sheathing proximate to the closed end of the protective sheathing and providing access into the interior of the protective sheathing,
said top slot having a width and a length, said width of the top slot being less than the width of the bottom slot, said top slot oriented substantially in alignment with the bottom slot, and said top slot being suitably adapted to accommodate the end of the surgical instrument such that the end of the surgical instrument is inserted through the top slot from the interior of the protective sheathing, a retention flap, said retention flap being substantially planar and having a top edge, a connection end opposite said top edge, and a face, said face being textured, said retention flap located within the interior of the protective sheathing proximate to the bottom slot and between the bottom slot and the open end of the protective sheathing, said retention flap being flexibly attached to the interior surface of the protective sheathing at its connection end, with the face of the retention flap oriented towards and substantially parallel to the closed end of the protective sheathing, said retention flap extending into the interior of the protective sheathing from the interior surface of the protective sheathing and oriented at an angle towards the closed end of the protective sheathing, such that the top edge and at least a portion of the face extend over at least a portion of the bottom slot, and said retention flap being suitably adapted to press at least a portion of its face against the surgical instrument and to be displaced towards the open end of the protective sheathing when the surgical instrument is inserted through the bottom slot and top slot, and at least one retention ridge, each said retention ridge located on the interior surface of the closed end of the protective sheathing, each said retention ridge being oriented substantially horizontally, with each said retention ridge extending into the interior of the protective sheathing from the interior surface of the closed end of the protective sheathing such that at least a portion of said retention ridge is aligned over at least a portion of the bottom slot;

whereby the surgical instrument protrudes through the bottom and top slots of the protective sheathing with the end of the surgical instrument protruding from the top slot.

* * * * *